United States Patent

Fushimi et al.

Patent Number: 5,225,206
Date of Patent: Jul. 6, 1993

[54] SUSTAINED-RELEASE PRANOPROFEN PREPARATION

[75] Inventors: Masunari Fushimi, Narashino; Hideyoshi Kanbe, Ichikawa; Shuichi Kasai, Narita; Akira Iwasa, Yotsukaido; Yoichi Sawayanagi, Tokyo, all of Japan

[73] Assignees: SS Pharmaceutical Co., Ltd.; Dojin Iyaku-Kako Co., Ltd., both of Tokyo, Japan

[21] Appl. No.: 830,919

[22] Filed: Feb. 4, 1992

[30] Foreign Application Priority Data

Feb. 8, 1991 [JP] Japan .................... 3-17769

[51] Int. Cl.⁵ .................... A61K 9/16; A61K 9/54; A61K 9/58
[52] U.S. Cl. .................... 424/490; 424/461; 424/462; 424/476; 424/479; 424/480; 424/491; 424/493; 424/494; 424/495; 424/496; 424/497; 424/498; 424/499; 424/500; 424/502; 424/482; 514/963
[58] Field of Search .................... 424/490, 491, 492

[56] References Cited

U.S. PATENT DOCUMENTS 4,971,805 11/1990 Kitanishi et al. .................... 424/494

FOREIGN PATENT DOCUMENTS 0433817 6/1991 European Pat. Off.
WO84/00490 2/1984 PCT Int'l Appl.

OTHER PUBLICATIONS

Chemical Abstracts, vol. 113, No. 10, 84872y, and JP-A-02-088519, Mar. 28, 1990.
Chemical Abstracts, vol. 110, No. 10, 82500q, and JP-A-63-079817, Sep. 4, 1988.
Chemical Abstracts, vol. 106, No. 22, 182682m, and JP-A-62-033116, Feb. 13, 1987.
Chemical Abstracts, vol. 114, No. 24, 235088w, and JP-A-03-041020, Feb. 21, 1991.

Primary Examiner—Thurman K. Page
Assistant Examiner—James M. Spear
Attorney, Agent, or Firm—Oblon, Spivak, McClelland, Maier & Neustadt

[57] ABSTRACT

A sustained-release pranoprofen preparation is disclosed. The preparation comprises an effective amount of pranoprofen and one or more sustained-release components selected from the group consisting of oily components, water-soluble components, water-insoluble components, and intestinally soluble components. It controls release of pranoprofen and lowers the maximum pranoprofen concentration in blood, maintaining its concentration in blood at a certain level for a long period of time. It reduces risks of side effects and can effectively treat diseases with dosing once or twice a day.

8 Claims, 5 Drawing Sheets

SUSTAINED-RELEASE PRANOPROFEN PREPARATION

BACKGROUND OF THE INVENTION

1. Field of the Invention

The present invention relates to a sustained-release pranoprofen preparation useful as an antipyretic, analgesic, or anti-inflammatory drug.

2. Description of the Background

Among non-steroidal anti-inflammatory drugs, propionic acid compounds typified by pranoprofen, ketoprofen, and ibuprofen exhibit excellently balanced antipyretic and anti-inflammatory effects with less side effects than other non-steroidal anti-inflammatory drugs. These drugs thus are widely used as a first drug of choice in clinics. Especially, pranoprofen is a superior anti-inflammatory drug with a minimal risk of side effects on gastrointestinal tract, which is common to non-steroidal anti-inflammatory drugs due to their special pharmaceutical actions.

A defect of pranoprofen is its short half-life period in blood, requiring the patients to dose the drug 3 times a day, which the patients sometimes feel difficulty to comply with. This is undesirable from the aspect of controlling diseases. Even if its side effect is small, a rapid concentration increase of a drug in blood after oral administration is by not necessarily means safe for patients. Development of a pranoprofen preparation which can safely deliver the effects of pranoprofen over a long period of time is therefore desired.

In view of this situation, the present inventors have undertaken extensive studies and found that the use of an oily component, water-soluble component, water-insoluble component, or intestinally soluble component, as sustained-release components, can effectively control the rate of release of pranoprofen. This finding has led to the completion of the present invention.

SUMMARY OF THE INVENTION

Accordingly, an object of the present invention is to provide a sustained-release pranoprofen preparation comprising an effective amount of pranoprofen and one or more sustained-release components selected from the group consisting of oily components, water-soluble components, water-insoluble components, and intestinally soluble components.

Other objects, features and advantages of the invention will hereinafter become more readily apparent from the following description.

DETAILED DESCRIPTION OF THE INVENTION AND PREFERRED EMBODIMENTS

In the sustained-release preparation of the present invention the sustained-release components selected from the group consisting of oily components, water-soluble components, water-insoluble components, and intestinally soluble components form a matrix or film, or both, by which the release of pranoprofen is retarded. Among the above components, oily components, water-soluble components, water-insoluble components, and intestinally soluble components can form a matrix; oily components, water-insoluble components, and intestinally soluble components can form a film. They may be used either individually or in combination in the sustained-release composition of the present invention.

Any oily components which can form a matrix or film and can retard the release of pranoprofen may be used for the purpose of the present invention, including, but not limited to, oils and fats, waxes, hydrocarbons, higher fatty acids, higher alcohols, esters, metal salts of higher fatty acid, and the like. Given as specific examples of oils and fats are vegetable oils such as cocoa butter, palm oil, Japan wax, coconut oil, and the like; animal oils such as beef tallow, lard, horse tallow, mutton tallow, and the like; hydrogenated oils derived from fish or animal oils such as hydrogenated fish oils, hydrogenated whale oil, hydrogenated beef tallow, and the like and hydrogenated oils derived from vegetable oils such as hydrogenated rapeseed oil, hydrogenated castor oil, hydrogenated coconut oil, hydrogenated soybean oil, and the like. Specific examples of waxes include plant waxes, e.g. carnauba wax, candelilla wax, bayberry wax, auricurry wax, espalt wax, etc.; animal waxes, e.g. yellow wax, white wax, insect wax, spermaceti, shellac, lanolin, etc.; and the like. Paraffin, petrolatum, microcrystalline wax, and the like, are given as specific examples of hydrocarbons. Given as specific examples of higher fatty acids are fatty acids having 8-32 carbon atoms, such as caprilic acid, undecanoic acid, lauric acid, tridecanoic acid, myristic acid, pentadecanoic acid, palmitic acid, malgaric acid, stearic acid, nonadecanoic acid, arachic acid, heneicosanoic acid, behenic acid, tricosanoic acid, lignoceric acid, pentacosanoic acid, cerotic acid, heptacosanoic acid, montanic acid, nonacosanoic acid, melissic acid, hentriacontanic acid, dotriacontanic acid, and the like. Specific examples of higher alcohols are higher alcohols having 12-32 carbon atoms such as lauryl alcohol, tridecyl alcohol, myristyl alcohol, pentadecyl alcohol, cetyl alcohol, heptadecyl alcohol, stearyl alcohol, nonadecyl alcohol, arachyl alcohol, behenyl alcohol, carnaubic alcohol, ceryl alcohol, corianyl alcohol, and myricyl alcohol. Specific examples of esters are fatty acid esters, e.g. myristyl palmitate, stearyl stearate, myristyl myristate, behenyl behenate, ceryl lignocerate, lacceryl cerotate, lacceryl laccerate, etc.; glycerine fatty acid esters, e.g. glyceril monolaurate, glyceril monomyristate, glyceril monostearate, glyceril monobehenate, glyceril monooleate, glyceril oleate stearate, glyceril dilaurate, glyceril dimyristate, glyceril distearate, glyceril trilaurate, glyceril trimyristate, glyceril tristearate, glyceril acetylstearate, glyceril trihydroxystearate, etc.; and the like. Specific examples of metal salts of higher fatty acid are calcium stearate, magnesium stearate, aluminum stearate, zinc stearate, zinc palmitate, zinc myristate, magnesium myristate, and the like.

Preferred water-soluble polymers are those which can form matrix and produce hydrogel in gastrointestinal tract. Specific examples include cellulose derivatives, e.g., methylcellulose, hydroxypropylcellulose, hydroxypropyl methylcellulose, carboxymethylcellulose sodium, etc; starch derivatives, e.g., sodium carboxymethyl starch, dextrin, pregelatinized starch, pullulan, etc.; vinyl derivatives, e.g., polyvinylpyrrolidone, carboxyvinyl polymer, polyvinyl alcohol, etc.; acrylic acid derivatives, e.g., polyacrylic acid, sodium polyacrylate, etc.; naturally occurring polymers and their derivatives, e.g.; acacia, tragacanth, locust bean gum, guar-gum, casein, karaya gum, pectin, arginic acid, agar, keratin, propylene glycol arginate, etc.; and the like.

As water-insoluble components, polymeric compounds which are different from common oily substances, but which form a matrix or a film can be used. Specific examples are microcrystalline cellulose, ethylcellulose, aminoalkyl methacrylate copolymer RS, cellulose acetate, polyvinyl acetate, polyvinyl chloride, and the like.

As specific examples of intestinally soluble components, polymeric compounds forming a matrix or a film and not soluble below the pH of stomach (about pH 4) but soluble in the pH range of 5.0-7.0, may be used. Specific examples are methacrylic acid copolymer S, methacrylic acid copolymer L, carboxymethyl ethylcellulose, purified shellac, hydroxymethylphthalate cellulose, hydroxypropylmethylcellulose phthalate, cellulose acetate phthalate, hydroxypropylmethylcellulose acetate succinate, methacrylic acid copolymer LD, cellulose acetate trimeritate, polyvinyl acetate phthalate, and the like.

The amounts of the above sustained-release components in the sustained-release pranoprofen composition of the present invention depend on the type of the preparation, the method of preparation, and the desired sustained-release characteristics, and the like. When they are used as a component for forming a matrix, an amount of 3-80% by weight, especially 4-70% by weight, in the total amount of the composition is preferable, and when used as a component for forming a film, an amount of 0.5-80% by weight, especially 2-40% by weight, is preferable.

Any base components commonly used for conventional pharmaceutical preparations, such as binders, lubricants, disintegrators, plasticizers, dissolution modifiers, excipients, and the like can be added to the preparation of the present invention.

There are no limitations as to forms of the preparation of the present invention so long as such forms are suitable for oral administration; it can be powders, granules, beads, tablets, capsules, or the like.

The sustained-release pranoprofen preparation of the present invention can be prepared, for example, (1) by adding sustained-release components in the form of solid, solution or suspension to pranoprofen, and preparing the mixture into any desired form according to a conventional method; or (2) by preparing a composition of pranoprofen and base components, followed by encapsulation of the composition into microcapsules by using sustained-release components or by covering of the composition with sustained-release components by a dry or wet method.

In order to further control the release rate of pranoprofen from the preparation prepared by the above method, it may be further coated with one or more of oily components, water-insoluble components, or intestinally soluble components. Furthermore, it is possible to combine two or more sustained-release pranoprofen preparations with different release rates; or in order to exhibit more rapid pharmaceutical effects after the administration, a preparation which is the mixture of the above sustained-release pranoprofen preparation and non-sustained-release pranoprofen preparation, or a preparation in which a sustained-release pranoprofen preparation and a non-sustained-release pranoprofen preparation are separately layered can be used. The amount of non-sustained-release pranoprofen to be formulated in such a preparation is usually such that the amount of pranoprofen in such a non-sustained-release preparation is in a range of 10-60% by weight, and preferably 15-50% by weight, of the total amount of pranoprofen contained in the preparation, although this proportion depends on a desired blood concentration, a period of time during which the pharmaceutical effects are required to last.

The sustained-release pranoprofen preparation thus obtained is capable of retarding the release of pranoprofen therefrom and maintaining its blood concentration at a certain level for a long period of time. Dosing once or twice a day can bring about the same effects as provided by several time dosing of conventional preparations, thus avoiding nuisance of frequent dosing and the reduction of clinical effects due to omission of dosing. The preparation of the present invention greatly improves the treating effects by pranoprofen by suppressing a rapid increase in blood concentration of this drug and by safely deriving the maximum effect of pranoprofen for a long period of time.

Other features of the invention will become apparent in the course of the following description of the exemplary embodiments which are given for illustration of the invention and are not intended to be limiting thereof.

EXAMPLES

| Example 1 | |
|---|---|
| Pranoprofen | 1,260.0 gm |
| Hydrogenated castor oil | 320.0 gm |
| Stearic acid | 320.0 0 gm |
| Microcrystalline cellulose | 300.0 gm |
| Total | 2,200.0 gm |

Purified water (720 gm) was added to the powder of the above components, and the mixture was kneaded and extruded from a extrusion granulator to obtain rod-shaped granules. The granules were rounded by a Marumerizer and dried at 55° C. for 3 hours. Beads thus prepared were sieved to obtain sustained-release beads (e) which passed through a 14 mesh sieve but not a 26 mesh sieve. Sustained-release beads (a) were blended with the following composition and compress-molded to prepare sustained-release tables (A); a tablet having a diameter of 9 mm and weighing 350 mg.

| Sustained-release beads (a) | 275.0 gm |
|---|---|
| Pranoprofen | 67.5 gm |
| Microcrystalline cellulose | 333.5 gm |
| Colloidal silicon dioxide | 7.0 gm |
| Magnesium stearate | 10.0 gm |
| Talc | 7.0 gm |
| Total | 700.0 gm |

EXAMPLE 2

600 gm of sustained-release beads (a) prepared in Example 1 were charged into a fluidized coating apparatus and spray-coated with 1,666 gm of a coating fluid having the following composition according to a conventional method to obtain sustained-release beads (b).

| Methacrylic acid copolymers S | 6.5% |
|---|---|
| Glycerine fatty acid ester | 0.5% |
| Talc | 0.2% |
| Ethyl alcohol | 92.8% |
| Total | 100.0% |

Sustained-release beads (b) were blended with components of the following composition and compress-molded to prepare sustained-release tablets (B); a tablet weighing 350 mg and having a diameter of 9 mm.

| Sustained-release beads (b) | 330.0 gm |
|---|---|
| Pranoprofen | 67.5 gm |
| Microcrystalline cellulose | 278.5 gm |
| Colloidal silicon dioxide | 7.0 gm |
| Magnesium stearate | 10.0 gm |
| Talc | 7.0 gm |
| Total | 700.0 gm |

EXAMPLE 3

300 gm of sustained-release beads (a) prepared in Example 1 were charged into a fluidized coating apparatus and spray-coated with 866 gm of a coating fluid having the following composition according to a conventional method to obtain sustained-release beads (c).

| Purified shellac | 4.5% |
|---|---|
| Castor oil | 0.5% |
| Talc | 0.2% |
| Ethyl alcohol | 94.8% |
| Total | 100.0% |

Sustained-release beads (c) were blended with components of the following composition and compress-molded to prepared sustained-release tablets (C); a tablet weighing 350 mg and having a diameter of 9 mm.

| Sustained-release beads (c) | 316.3 gm |
|---|---|
| Pranoprofen | 67.5 gm |
| Microcrystalline cellulose | 292.2 gm |
| Colloidal silicon dioxide | 7.0 gm |
| Magnesium stearate | 10.0 gm |
| Talc | 7.0 gm |
| Total | 700.0 gm |

EXAMPLE 4

Sustained-release beads (a) prepared in Example 1 and sustained-release beads (b) prepared in Example 2 were blended with components of the following composition and compress-molded to prepare sustained-release tablets (D); a tablet weighing 350 mg and having a diameter of 9 mm.

| Sustained-release beads (a) | 137.5 gm |
|---|---|
| Sustained-release beads (b) | 165.0 gm |
| Pranoprofen | 67.5 gm |
| Microcrystalline cellulose | 306.0 gm |
| Colloidal silicon dioxide | 7.0 gm |
| Magnesium stearate | 10.0 gm |
| Talc | 7.0 gm |
| Total | 700.0 gm |

EXAMPLE 5

150 gm of sustained-release beads (a) prepared in Example 1 were charged into CF-granulator (trademark, manufactured by Fueund International Ltd.) and spray-coated with 658.5 gm of a coating fluid having the following composition according to a conventional method to obtain sustained-release beads (d).

| Pranoprofen | 4.0% |
|---|---|
| Hydroxypropyl cellulose | 1.0% |
| Talc | 0.2% |
| Ethyl alcohol | 94.8% |
| Total | 100.0% |

| Example 6 | |
|---|---|
| Pranoprofen | 360.0 gm |
| Microcrystalline cellulose | 632.0 gm |
| Total | 992.0 gm |

Purified water (753 gm) was added to the powder of the above components, and the mixture was kneaded and extruded from a extrusion granulator to obtain rod-shaped granules. The granules were rounded by a Marumerizer and dried at 55° C. for 3 hours. Beads thus prepared were sieved to obtain sustained-release beads (e) which passed through a 14 mesh sieve but not a 26 mesh sieve.

| Example 7 | |
|---|---|
| Pranoprofen | 900.0 gm |
| Microcrystalline cellulose | 260.0 gm |
| Total | 1160.0 gm |

A solution of hydroxypropylmethyl cellulose (45 gm) dissolved in 405 gm of purified water was added to the powder of the above components, and the mixture was kneaded and extruded from a extrusion granulator to obtain rod-shaped granules. The granules were rounded by a Marumerizer and dried at 55° C. for 5 hours. Beads thus prepared were sieved to obtain sustained-release beads (f) which passed through a 14 mesh sieve but not a 26 mesh sieve.

EXAMPLE 8

300 gm of sustained-release beads (f) prepared in Example 7 were charged into a fluidized coating apparatus and spray-coated with 71.6 gm of a coating fluid having the following composition according to a conventional method to obtain sustained-release beads (g).

| Aminoalkyl methacrylate copolymer RS | 14.0% |
|---|---|
| Triethyl citrate | 4.2% |
| Colloidal silicon dioxide | 2.8% |
| Purified water | 79.0% |
| Total | 100.0% |

| Example 9 | |
|---|---|
| Pranoprofen | 630.0 gm |
| Hydrogenated castor oil | 400.0 gm |
| Total | 1030.0 gm |

A solution of hydroxypropylmethyl cellulose (50 gm) dissolved in 450 gm of purified water was added to the powder of the above components, and the mixture was kneaded and extruded from a extrusion granulator to obtain rod-shaped granules. The granules were rounded by a Marumerizer and dried at 55° C. for 3 hours. Beads thus prepared were sieved to obtain sustained-release beads (h) which passed through a 14 mesh sieve but not a 26 mesh sieve.

| Example 10 | |
|---|---|
| Pranoprofen | 112.5 gm |
| Methylcellulose | 420.0 gm |
| Lactose | 150.0 gm |
| Colloidal silicon dioxide | 7.0 gm |
| Magnesium stearate | 3.5 gm |
| Talc | 7.0 gm |
| Total | 700.0 gm |

The powder mixture of the above composition was compress-molded to prepare sustained-release tablets (E); a tablet weighing 350 mg and having a diameter of 9 mm.

| Example 11 | |
|---|---|
| Pranoprofen | 640.0 gm |
| Corn starch | 240.0 gm |
| Total | 880.0 gm |

The above powder mixture was pulverized and granulated by a rotating granulator using 350 gm of 24-32-mesh non-pareil seeds as a core while applying a solution of 62.5 gm of purified shellac dissolved in 1,187.5 gm of ethyl alcohol. The beads thus obtained were dried at 55° C for 2 hours and were sieved to obtain sustained-release beads (i) which passed through a 14 mesh sieve but not a 26 mesh sieve.

| Example 12 | |
|---|---|
| Pranoprofen | 2364.0 gm |
| Corn starch | 1260.0 gm |
| Total | 3624.0 gm |

The above powder mixture was granulated by a rotating granulator using 1,260 gm of 28-35 mesh purified sucrose as a core while applying a solution of 105 gm of hydroxypropyl cellulose dissolved in 1,995 gm of 50% ethyl alcohol. The beads thus obtained were dried at 55° C. for 2 hours and sieved to obtain non-coated beads (j) which passed through a mesh sieve but not a 26 mesh sieve.

300 gm of beads (j) thus prepared were charged into a fluidized coating apparatus and spray-coated with 1,042 gm of a coating fluid having the following composition according to a conventional method to obtain sustained-release beads (k).

| Methacrylic acid copolymer L | 6.5% |
|---|---|
| Glycerine fatty acid ester | 0.5% |
| Talc | 0.2% |
| Ethyl alcohol | 92.8% |
| Total | 100.0% |

EXAMPLE 13

300 gm of beads (j) prepared in Example 12 were charged into a fluidized coating apparatus and spray-coated with 1,042 gm of a coating fluid having the following composition according to a conventional method to obtain sustained-release beads (m).

| Methacrylic acid copolymers S | 6.5% |
|---|---|
| Glycerine fatty acid ester | 0.5% |
| Talc | 0.2% |
| Ethyl alcohol | 92.8% |
| Total | 100.0% |

EXAMPLE 14

300 gm of beads (j) prepared in Example 12 were charged into a fluidized coating apparatus and spray-coated with 1,210 gm of a coating fluid having the following composition according to a conventional method to obtain sustained-release beads (n).

| Hydroxypropylmethylcellulose phthalate | 6.0% |
|---|---|
| Talc | 0.2% |
| Purified water | 18.8% |
| Ethyl alcohol | 75.0% |
| Total | 100.0% |

EXAMPLE 15

500 gm of beads (j) prepared in Example 12 were charged into a fluidized coating apparatus and spray-coated with 375 gm of a coating fluid having the following composition according to a conventional method to obtain sustained-release beads (p).

| White wax | 10.0% |
|---|---|
| Glyceril monostearate | 10.0% |
| Talc | 30.0% |

| | |
|---|---|
| Isopropyl alcohol | 50.0% |
| Total | 100.0% |

EXAMPLE 16

400 gm of beads (j) prepared in Example 12 were charged into a fluidized coating apparatus and spray-coated with 1,800 gm of a coating fluid having the following composition according to a conventional method to obtain sustained-release beads (q).

| | |
|---|---|
| Aminoalkyl methacrylate copolymer RS | 3.2% |
| Glycerine fatty acid ester | 0.3% |
| Talc | 0.5% |
| Ethyl alcohol | 94.0% |
| Total | 100.0% |

EXAMPLE 17

300 gm of beads (j) prepared in Example 12 were charged into a fluidized coating apparatus and spray-coated with 1,317 gm of a coating fluid having the following composition according to a conventional method to obtain sustained-release beads (r).

| | |
|---|---|
| Aminoalkyl methacrylate copolymer RS | 2.2% |
| Polyvinylpyrrolidone | 1.1% |
| Glycerine fatty acid ester | 0.3% |
| Talc | 0.5% |
| Ethyl alcohol | 95.9% |
| Total | 100.0% |

Sustained-release beads (r) were mixed with following other components and compress-molded to prepare sustained-release tablets (F); two tablets weighting 400 mg and each tablet having a diameter of 8 mm.

| | |
|---|---|
| Sustained-release beads (r) | 209.4 gm |
| Microcrystalline cellulose | 185.6 gm |
| Colloidal silicon dioxide | 4.0 gm |
| Magnesium stearate | 1.0 gm |
| Total | 400.0 gm |

EXAMPLE 18

300 gm of beads (j) prepared in Example 12 were charged into a fluidized coating apparatus and spray-coated with 1,317 gm of a coating fluid having the following composition according to a conventional method to obtain sustained-release beads (s).

| | |
|---|---|
| Aminoalkyl methacrylate copolymer RS | 1.1% |
| Methacrylic acid copolymers S | 1.1% |
| Hydroxypropyl cellulose | 1.1% |
| Glycerine fatty acid ester | 0.3% |
| Talc | 0.5% |
| Ethyl alcohol | 95.9% |
| Total | 100.0% |

Sustained-release beads (s) were mixed with the following other components and compress-molded to prepare sustained-release tablets (G); two tablets weighting 400 mg and each tablet having a diameter of 8 mm.

| | |
|---|---|
| Sustained-release beads (s) | 209.4 gm |
| Microcrystalline cellulose | 185.6 gm |
| Colloidal silicon dioxide | 4.0 gm |
| Magnesium stearate | 1.0 gm |
| Total | 400.0 gm |

EXAMPLE 19

300 gm of beads (j) prepared in Example 12 were charged into a fluidized coating apparatus and spray-coated with 143 gm of a coating fluid having the following composition according to a conventional method to obtain sustained-release beads (t).

| | |
|---|---|
| Ethylcellulose | 1.5% |
| Polyvinylpyrrolidone | 0.5% |
| Talc | 0.1% |
| Ethyl alcohol | 97.9% |
| Total | 100.0% |

EXAMPLE 20

500 gm of beads (p) prepared in Example 15 were charged into a fluidized coating apparatus and spray-coated with 1,736 gm of a coating fluid having the following composition according to a conventional method to obtain sustained-release beads (u).

| | |
|---|---|
| Methacrylic acid copolymers S | 6.5% |
| Glycerine fatty acid ester | 0.5% |
| Talc | 0.2% |
| Ethyl alcohol | 92.8% |
| Total | 100.0% |

| Example 21 | |
|---|---|
| Pranoprofen | 33.9 gm |
| Polyethylene glycol 600 | 10.2 gm |
| Ethylcellulose | 101.6 gm |
| Total | 145.7 gm |

The above components were dissolved into 2,850 gm of ethyl alcohol. Colloidal silicon dioxide (4.4 gm) was dispersed in the solution thus obtained. The mixture was spray-dried according to a conventional method to obtain sustained-release powder (v). The powder (v) was compress-molded together with other components shown below to prepare sustained-release tablets (H); two tablets weighing 517 mg and a tablet having a diameter of 8 mm.

| | |
|---|---|
| Sustained-release powder (v) | 150.1 gm |
| Croscarmellose sodium | 3.5 gm |
| Colloidal silicon dioxide | 0.8 gm |
| Magnesium stearate | 0.7 gm |
| Talc | 0.7 gm |
| Total | 155.8 gm |

TEST EXAMPLE 1

Figure 1:
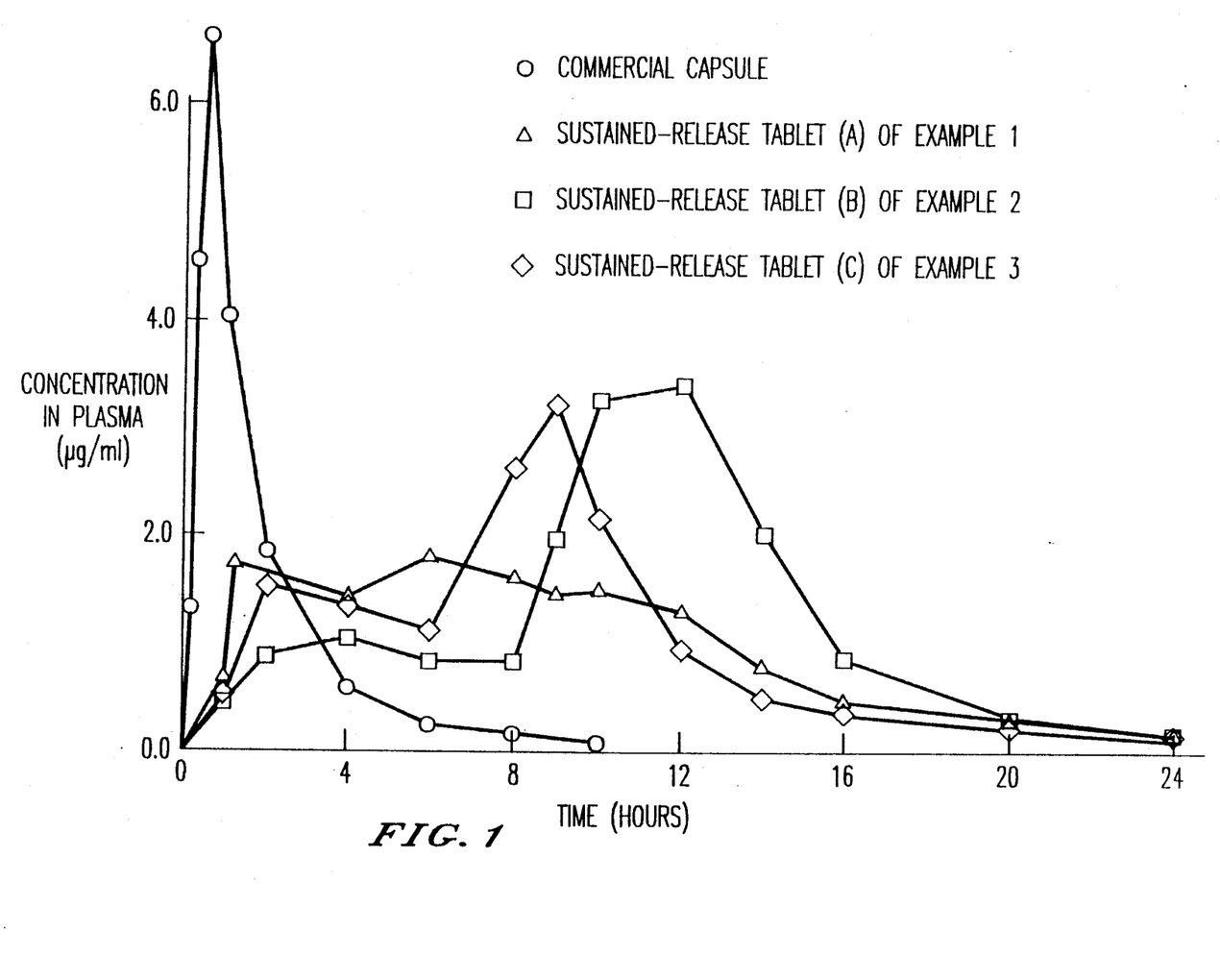
FIG. 1 is a drawing showing the relationship between the concentration of pranoprofen in plasma and time according to Test Example 1.
Figure 2:
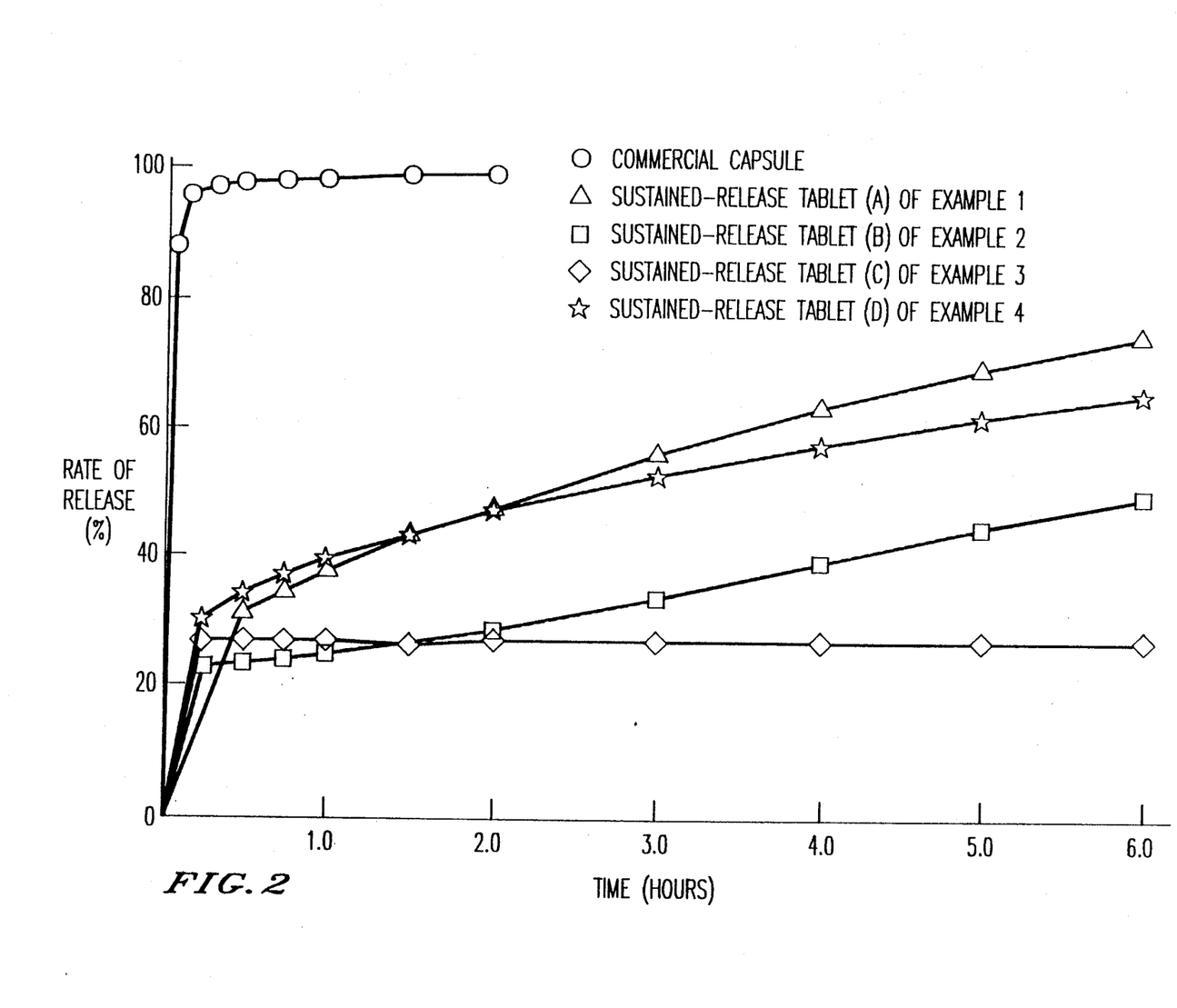
FIG. 2 is a drawing showing the results of dissolution test according to Test Example 2, in which is shown the rate of dissolution of pranoprofen over time from the sustained-release pranoprofen preparations in which rapid-release pranoprofen and sustained-release pranoprofen are mixed.
Figure 3:
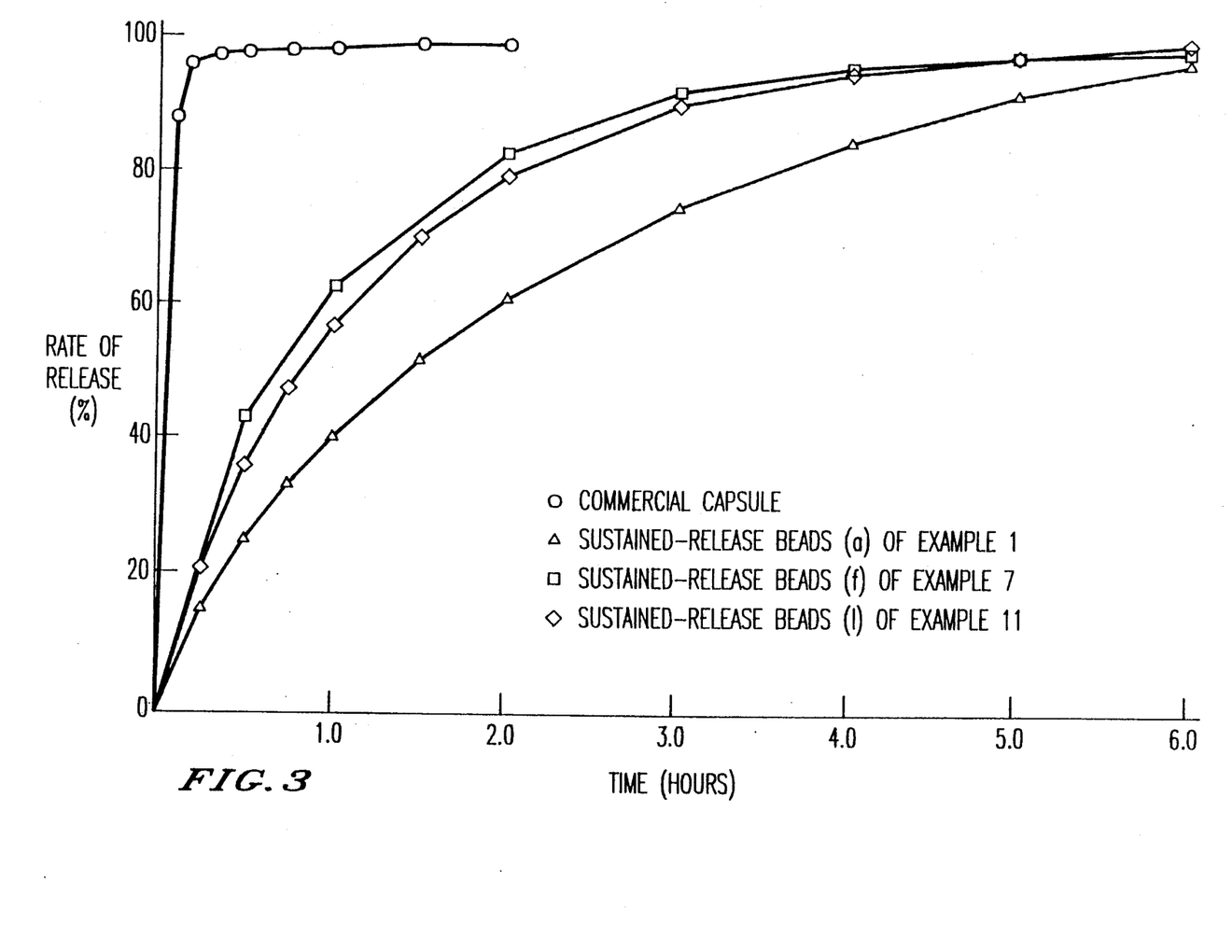
FIG. 3 is a drawing showing the results of dissolution test according to Test Example 2, in which is shown the rate of dissolution of pranoprofen over time from the sustained-release pranoprofen preparations from which the release of pranoprofen is sustained by a matrix-forming component.
Figure 4:
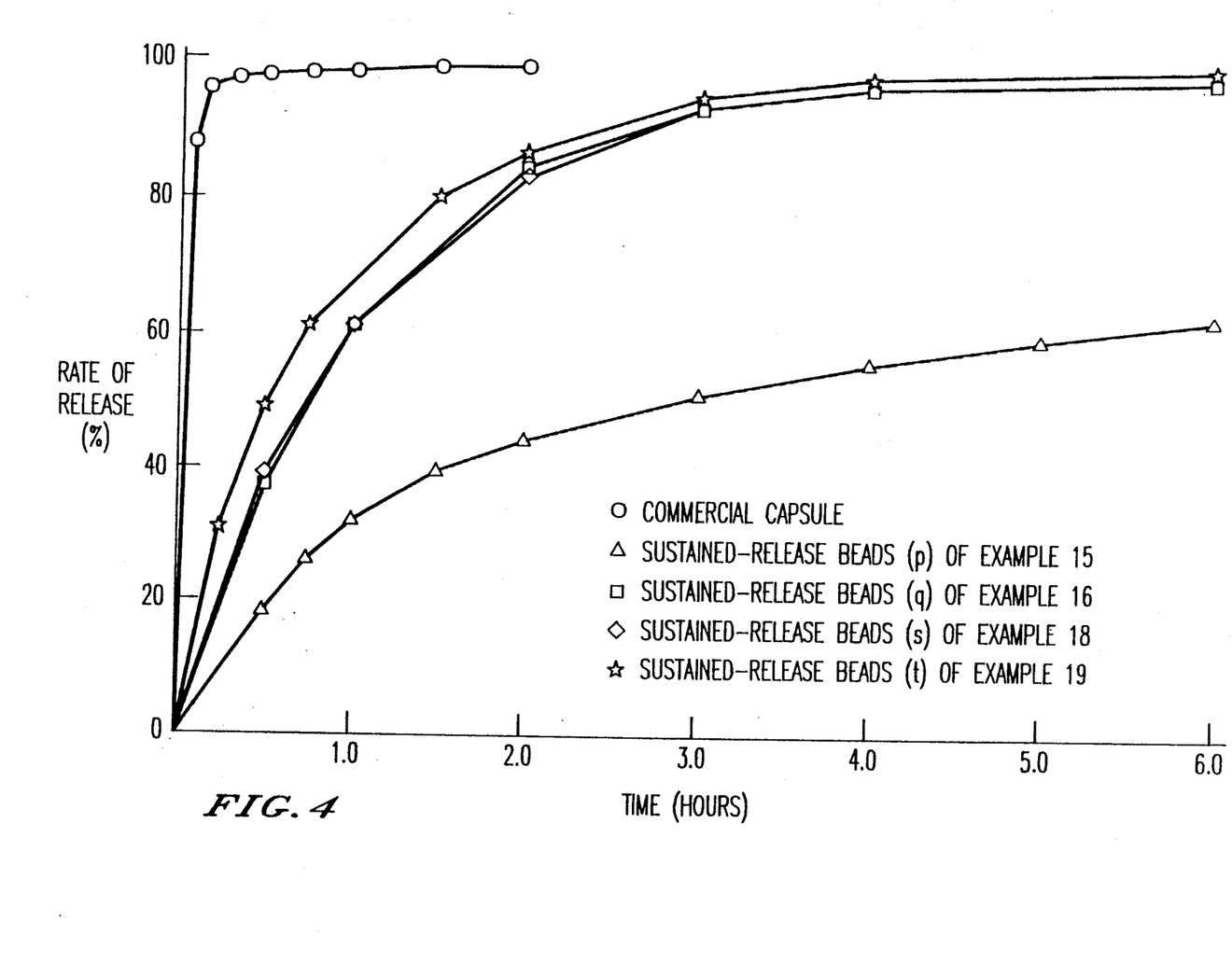
FIG. 4 is a drawing showing the results of dissolution test according to Test Example 2, in which is shown the rate of dissolution of pranoprofen over time from the sustained-release pranoprofen preparations from which the release of pranoprofen is sustained by a film-forming component.
Figure 5:
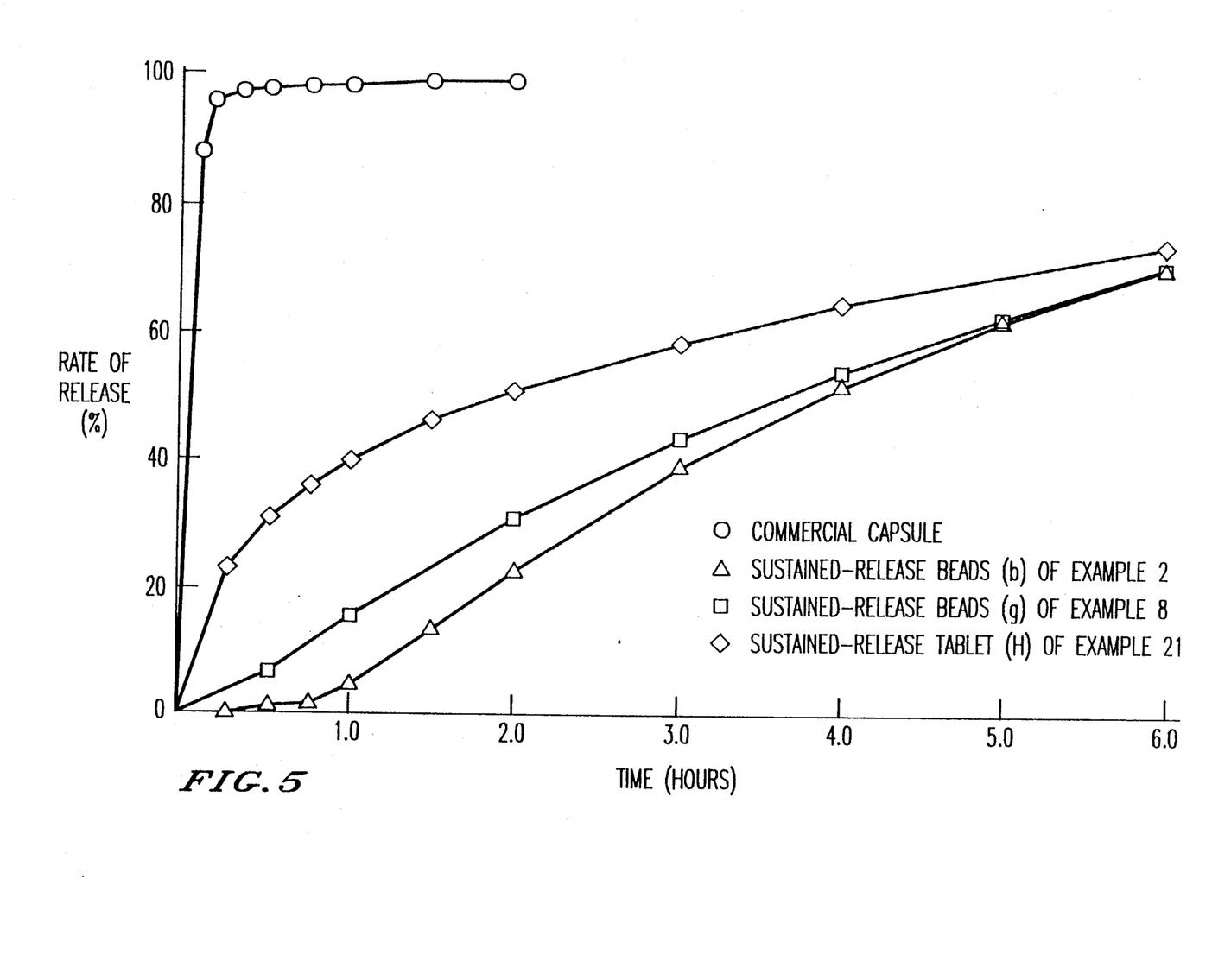
FIG. 5 is a drawing showing the results of dissolution test according to Test Example 2, in which are shown the rate of dissolution of pranoprofen over time from the sustained-release pranoprofen preparations from which the release of pranoprofen is sustained by a microcapsule comprising a film-forming component; and the rate of dissolution of pranoprofen over time from the sustained-release pranoprofen preparations from which the release of pranoprofen is sustained by matrix-forming components and film-forming components.

Two (2) tablets (pranoprofen content: 225 mg), each from sustained-release tablets A, B, and C prepared in Examples 1-3, and a commercially available conventional capsule (pranoprofen content: 75 mg) were administered to healthy male adults (each sample to 3 persons) together with 180 ml of water 30 minutes after meal. The concentration of pranoprofen in plasma was measured over time by high performance liquid chromatography. The results are shown in FIG. 1, which demonstrates that sustained-release tablets A–C of the present invention maintained a certain level of pranoprofen plasma concentration for a long period of time without lowering its bioavailability.

TEST EXAMPLE 2

Dissolution of pranoprofen from sustained-release pranoprofen preparations of the present invention and from a commercially available conventional capsule was measured by the rotation paddle method (The Pharmacopeia of Japan, 11th edition) using a buffer test solution of pH 6.8. The results are shown in FIGS. 2–5, which demonstrates the controlled release rate of pranoprofen from the preparation of the present invention as compared with the dissolution from the conventional available capsule.

Obviously, numerous modifications and variations of the present invention are possible in light of the above teachings. It is therefore to be understood that within the scope of the appended claims, the invention may be practiced otherwise than as specifically described herein.

What is claimed is:

1. A sustained-release pranoprofen preparation comprising pranoprofen and an oily component selected from the group consisting of oils, fats, waxes, hydrocarbons, higher fatty acids, higher alcohols having 12–32 carbon atoms, fatty acids esters, glycerine fatty acid esters and metal salts of higher fatty acids; and a coating of one or more components selected from the group consisting of polymeric water-insoluble components and polymeric intestinally soluble components.

2. A sustained-release pranoprofen preparation comprising (i) beads comprising pranoprofen and an oily component selected from the group consisting of oils, fats, waxes, hydrocarbons, higher fatty acids, higher alcohols having 12–32 carbon atoms, fatty acid esters, glycerine fatty acid esters and metal salts of higher fatty acids, said beads being coated by one or more components selected from the group consisting of polymeric water-insoluble components and polymeric intestinally soluble components (ii) a mixture of pranoprofen and one or more components selected from the group consisting of binders, lubricants, disintegrators, dissolution modifiers, and excipients.

3. The sustained-release pranoprofen preparation according to claim 1, wherein said beads are coated with one or more components selected from said oily components, polymeric water-insoluble components, or polymeric intestinally soluble components.

4. The sustained-release pranoprofen preparation according to claim 2, wherein said beads are coated with one or more components selected from said oily components, polymeric water-insoluble components, or polymeric intestinally soluble components.

5. The sustained-release pranoprofen preparation according to claim 3, wherein said coating components further comprise pranoprofen.

6. The sustained-release pranoprofen preparation according to claim 4, wherein said coating components further comprise pranoprofen.

7. A sustained-release pranoprofen preparation comprising (a) beads comprising pranoprofen and an oily component selected from the group consisting of oils, fats, waxes, hydrocarbons, higher fatty acids, higher alcohols having 12–32 carbon atoms, fatty acid esters, glycerine fatty acid esters and metal salts of higher fatty acids, (b) beads comprising pranoprofen and said oily component coated with one or more components selected from oily components, polymeric water-insoluble components, or polymeric intestinally soluble components, and (c) a mixture of pranoprofen and one or more components selected from the group consisting of binders, lubricants, disintegrators, dissolution modifiers and excipients.

8. The sustained-release pranoprofen preparation according to claim 7, wherein said coating components further comprise pranoprofen.

* * * * *